United States Patent [19]
Brunner et al.

[11] Patent Number: 5,248,683
[45] Date of Patent: Sep. 28, 1993

[54] BENZO-1,2,3-THIADIAZOLE DERIVATIVES

[75] Inventors: Hans-Georg Brunner, Lausen; Walter Kunz, Oberwil; Rolf Schurter, Binningen, all of Switzerland

[73] Assignee: Ciba-Geigy Corporation, Ardsley, N.Y.

[21] Appl. No.: 893,292

[22] Filed: Jun. 4, 1992

[30] Foreign Application Priority Data

Jun. 5, 1991 [CH] Switzerland .................. 1668/91

[51] Int. Cl.$^5$ ............... C07D 413/06; C07D 411/06; C07D 409.06; C07D 417/06; A01N 43/86; A01N 43/82; A01N 43/54

[52] U.S. Cl. .................................. 514/270; 514/186; 514/211; 514/212; 514/218; 514/227.2; 514/228.8; 514/269; 514/322; 514/361; 540/452; 540/454; 540/460; 540/486; 540/488; 540/492; 540/524; 544/4; 544/54; 544/64; 544/96; 544/225; 544/226; 544/300; 544/319; 546/199; 548/101; 548/126

[58] Field of Search ............... 548/126, 126, 101; 544/319, 225, 226, 300, 319; 540/460, 510, 452, 486, 488, 460, 492, 454, 524; 514/269, 218, 183, 186, 211, 212, 227.2, 228.8, 218, 269, 322, 270, 361; 71/90; 546/199

[56] References Cited

U.S. PATENT DOCUMENTS

| | | | |
|---|---|---|---|
| 3,880,874 | 4/1975 | Beard | 548/126 |
| 4,931,581 | 6/1990 | Schurter | 560/18 |
| 4,946,981 | 8/1990 | Carter | 558/415 |
| 5,051,436 | 9/1991 | Kunz | 514/361 |
| 5,066,661 | 11/1991 | Kunz | 514/361 |

FOREIGN PATENT DOCUMENTS 1177972 1/1970 United Kingdom.

*Primary Examiner*—Patricia L. Morris
*Attorney, Agent, or Firm*—Edward McC. Roberts; Marla J. Mathias

[57] ABSTRACT

Compounds of the formula

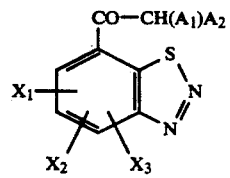

in which
$A_1$ and $A_2$ independently of one another are CO—C$_1$-C$_4$alkyl, COO—C$_1$-C$_4$alkyl, CO—CF$_3$, CO—N(R)$_2$ or cyano;
$A_1$ and $A_2$ together are CO(X)$_n$—C$_1$-C$_3$alkylene-(X)$_n$CO, CO(X)$_n$—C$_1$-C$_3$alkylene-(X)$_n$CO which is substituted by C$_1$-C$_4$alkyl, COOR, CON(R)$_2$, cyano or phenyl, it being possible for the phenyl ring, in turn, to be substituted by halogen, methyl, trifluoromethyl, methoxy, nitro or cyano; CO—N(R)—CO—N(R)—CO;
R is hydrogen, C$_1$-C$_6$alkyl, C$_3$-C$_6$alkenyl or C$_3$-C$_6$alkynyl;
X is oxygen, sulfur or N(CH$_3$);
$X_1$, $X_2$ and $X_3$ independently of one another are hydrogen, halogen, methyl, methylthio, methoxy or nitro;
n is 0 or 1;
including the salts of the compounds of the formula I with agriculturally acceptable organic or inorganic bases, and including the metal complexes; have valuable microbicidal properties.

The novel compounds can be used in crop protection for preventing the attack of crop plants by phytopathogenic microorganisms and for the control of these pests.

21 Claims, No Drawings

BENZO-1,2,3-THIADIAZOLE DERIVATIVES

The present invention relates to novel substituted benzo-1,2,3-thiadiazole derivatives of the formula I below. The invention furthermore relates to the preparation of these substances and the compositions comprising at least one of these compounds as active ingredients. Moreover, the invention relates to the preparation of the abovementioned compositions and to the use of the active ingredients or of the compositions for protecting plants against attack by harmful microorganisms, in particular plant-injurious fungi.

The compounds according to the invention are those of the general formula I

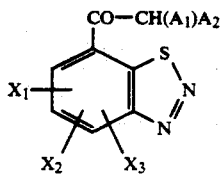

in which $A_1$ and $A_2$ independently of one another are $CO-C_1-C_4$alkyl, $COO-C_1-C_4$alkyl, $CO-CF_3$, $CO-N(R)_2$ or cyano;

$A_1$ and $A_2$ together are $CO(X)_n-C_1-C_3$alkylene-$(X)_nCO$, $CO(X)_n-C_1-C_3$alkylene-$(X)_nCO$ which is substituted by $C_1-C_4$alkyl, COOR, CON(R)$_2$, cyano or phenyl, it being possible for the phenyl ring, in turn, to be substituted by halogen, methyl, trifluoromethyl, methoxy, nitro or cyano; $CO-N(R)-CO-N(R)-CO$;

R is hydrogen, $C_1-C_6$alkyl, $C_3-C_6$alkenyl or $C_3-C_6$alkynyl;

X is oxygen, sulfur or N(CH$_3$);

$X_1$, $X_2$ and $X_3$ independently of one another are hydrogen, halogen, methyl, methylthio, methoxy or nitro;

n is 0 or 1;

including the salts of the compounds of the formula I with agriculturally acceptable organic or inorganic bases, and including the metal complexes.

Halogen is fluorine, chlorine, bromine or iodine, preferably fluorine, and furthermore in the sequence chlorine, bromine and iodine. As substituent in individual radicals, halogen can be represented up to 3 times.

Alkyl itself or as a component of another substituent is to be understood as meaning straight-chain and branched alkyl radicals. Depending on the number of the carbon atoms given, they are, for example, the following preferred groups: methyl, ethyl and the isomers of propyl or butyl, for example isopropyl, isobutyl, tert-butyl or sec-butyl.

Alkenyl is, for example, prop-1-enyl, allyl, but-1-enyl, but-2-enyl or but-3-enyl, and alkynyl is, for example, prop-2-ynyl, but-1-ynyl, pent-4-ynyl or hex-2-ynyl.

The invention relates to the free compounds of the formula I as well to the acid addition salts thereof with inorganic and organic bases, or complexes thereof with metal salts.

Salts according to the invention are, in particular, salts with physiologically acceptable inorganic and organic bases, depending on the intended use, for example the hydroxides, oxides, carbonates, hydrogen carbonates or amines of alkali metals or alkaline earth metals, such as mono-, di- or trialkyl amines, or heterocyclic bases such as pyridine bases (for example pyridine, 4-dimethylaminopyridine, collidine), or else addition salts with suitable salts, for example magnesium chloride or calcium chloride.

Metal complexes of the formula I are composed of the organic molecule on which they are based and an inorganic or organic metal salt, for example, inter alia, the halides, nitrates, sulfates, phosphates and tartrates of magnesium, calcium, barium, tin, copper, manganese, iron, zinc and nickel, and also of other metals. The metal cations can assume the valencies which are possible.

Due to their particular crop-protecting properties, the active ingredients of the formula I can be classified as follows:

a) Compounds of the formula I in which $A_1$ and $A_2$ together are $CO(X)_n-C_1-C_3$alkylene-$(X)_nCO$, or $CO-C_1-C_3$alkylene-$CO$ which is substituted by $C_1-C_4$alkyl, COOH, COOCH$_3$, COOC$_2$H$_5$, COOCH$_2$-CH=CH$_2$, COOCH$_2-C\equiv CH$, phenyl, the group $CO-N(CH_3)_2$ or cyano; $CO-N(R')-CO-N(R')-CO$; X is oxygen or sulfur;

R' is hydrogen or $C_1-C_3$alkyl;

$X_1$, $X_2$ and $X_3$ independently of one another are hydrogen, F, methyl, methoxy, methylthio or nitro;

n is 0 or 1;

including the salts of the compounds of the formula I with organic or inorganic bases as well as the metal complexes with Mg, Ca, Ba, Cu, Sn, Fe, Zn, Cu, Ni or Mn.

b) Compounds of the formula I in which:

$A_1$ and $A_2$ independently of one another are $CO-C_1-C_4$alkyl, $COO-C_1-C_4$alkyl, $CO-CF_3$, $CO-N(R)_2$ or cyano;

R is hydrogen, $C_1-C_6$alkyl, $C_3-C_6$alkenyl or $C_3-C_6$alkynyl;

$X_1$, $X_2$, and $X_3$ independently of one another are hydrogen, halogen, methyl, methylthio, methoxy or nitro;

including the salts of the compounds of the formula I with agriculturally acceptable organic or inorganic bases as well as the metal complexes with Mg, Ca, Ba, Cu, Sn, Fe, Zn, Ni or Mn.

a$_1$) Compounds of the formula I in which:

$A_1$ and $A_2$ together are $CO(X)_n-C_1-C_3$alkylene-$(X)_nCO$, or $CO(X)_n-C_1-C_3$alkylene-$(X)_nCO$ which is substituted by $C_1-C_4$alkyl, COOH, COOCH$_3$, phenyl or the group $CO-N(CH_3)_2$;

X is oxygen;

$X_1$, $X_2$, and $X_3$ independently of one another are hydrogen, fluorine or methyl;

n is 0 or 1.

b$_1$) Compounds of the formula I in which:

$A_1$ and $A_2$ independently of one another are $CO-C_1-C_2$alkyl, $COO-C_1-C_2$alkyl, $CO-CF_3$ or $CO-N(R)_2$;

$X_1$, $X_2$, and $X_3$ independently of one another are hydrogen, fluorine or methyl.

a$_2$) Compounds of the formula I in which:

$A_1$ and $A_2$ together are $CO-C_1-C_3$alkylene-CO, or $CO-C_1-C_3$alkylene-CO which is substituted by $C_1-C_2$alkyl, COOH or phenyl;

$X_1$, $X_2$, and $X_3$ independently of one another are hydrogen or fluorine.

b$_2$) Compounds of the formula I in which:

$A_1$ and $A_2$ independently of one another are $CO-C_1-C_2$alkyl, $COO-C_1-C_2$alkyl or $CO-N(CH_3)_2$;

$X_1$, $X_2$, and $X_3$ independently of one another are hydrogen or fluorine.

a3) Compounds of the formula I in which:

$A_1$ and $A_2$ together are CO—$C_1$-$C_3$alkylene-CO, or CO—$C_1$-$C_3$alkylene-CO which is substituted by methyl;

$X_1$, $X_2$ and $X_3$ independently of one another are hydrogen or fluorine.

b3) Compounds of the formula I in which:

$A_1$ and $A_2$ independently of one another are CO—$CH_3$, $COOC_1$-$C_4$alkyl, CN or $CON(CH_2C\equiv CH)_2$;

$X_1$, $X_2$, and $X_3$ independently of one another are hydrogen or fluorine.

a4) Compounds of the formula I in which:

$A_1$ and $A_2$ together are CO—N(R')—CO—N(R')—CO;

R' is hydrogen or $C_1$-$C_3$alkyl;

$X_1$, $X_2$ and $X_3$ independently of one another are hydrogen, fluorine or methyl.

a5) Compounds of the formula I in which:

$A_1$ and $A_2$ together are CO—$N(CH_3)$—CO—$N(CH_3)$—CO;

$X_1$, $X_2$ and $X_3$ independently of one another are hydrogen or fluorine.

The following active ingredients of the formula I are distinguished by particularly advantageous crop-protecting properties:

2(benzo-1,2,3-thiadiazole-7-carbonyl)-3-hydroxy-cyclohex-2-enone;

2-(benzo-1,2,3-thiadiazole-7-carbonyl)-3-hydroxy-5,5-dimethyl-cyclohex-2-enone;

2-(benzo-1,2,3-thiadiazole-7-carbonyl)-3-hydroxy-5-methyl-cyclohex-2-enone;

2-(benzo-1,2,3-thiadiazole-7-carbonyl)-3-hydroxy-5-isopropyl-cyclohex-2-enone;

2-(benzo-1,2,3-thiadiazole-7-carbonyl)-3-hydroxy-5-phenyl-cyclohex-2-enone;

2-(6-fluoro-benzo-1,2,3-thiadiazole-7-carbonyl)-3-hydroxy-5,5-dimethyl-cyclohex-2-enone;

2-(4-fluoro-benzo-1,2,3-thiadiazole-7-carbonyl)-3-hydroxy-cyclohex-2-enone;

5-(benzo-1,2,3-thiadiazole-7-carbonyl)-1,3-dimethyl-2,4,6-1H,3H,5H-pyrimidinetrione; diethyl (benzo-1,2,3-thiadiazole-7-carbonyl)malonate.

The compounds of the formula I are prepared as follows:

a) by acylation of methylene compounds of the formula II

$A_1$—$CH_2$—$A_2$ (II)

with an activated acid derivative of the formula III

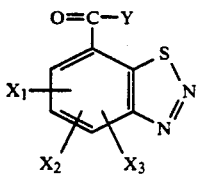

(III)

in the presence of a base with or without an addition of metal salts, for example $MgCl_2$ or MgO, or a Lewis acid in inert solvents at temperatures of from −30° C. to 180° C., preferably 0° to 130° C.; where Y is halogen, cyano or the radical

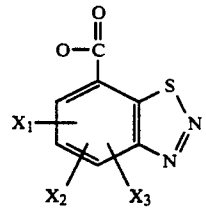

and $A_1$, $A_2$, $X_1$, $X_2$ and $X_3$ are as defined in formula I; or b) from methylene compounds of the formula IIa

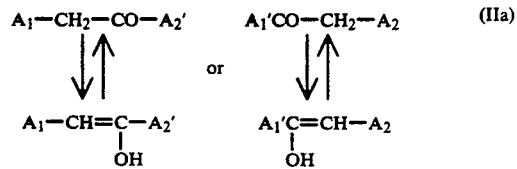

(IIa)

by acylation of the enol form on the oxygen atom with a compound of the formula III

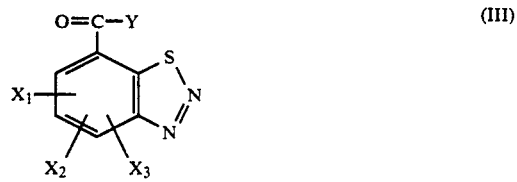

(III)

in the presence of a base in an inert solvent at temperatures of from −30° C. to 160° C. via the intermediates of the formula IV

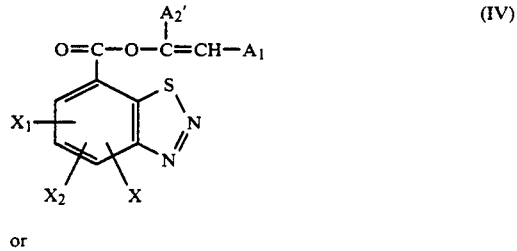

(IV)

in which $A_1'$ and $A_2'$, respectively, are defined as follows:

$C_1$-$C_4$alkyl, O—$C_1$-$C_4$alkyl, $CF_3$, $N(R)_2$, or $(X)_n$—$C_1$-$C_3$alkylene-$(X)_n$CO which is unsubstituted or substituted by $C_1$-$C_4$alkyl, COOR, $CON(R)_2$, cyano or phenyl, in which the phenyl ring, in turn, can be substituted by halogen, methyl, trifluoromethyl, methoxy, nitro or cyano; and N(R)—CO—N(R)—CO;

and by rearranging these products with a base with or without an addition of cyanide compounds or of a Lewis acid, for example, $AlCl_3$, as catalyst in inert solvents at temperatures of from −30° C. to 160° C., preferably 0° to 120° C., to give compounds of the formula Ia

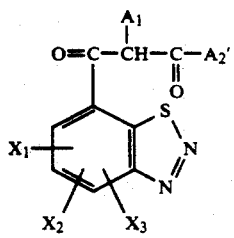

(Ia)

or

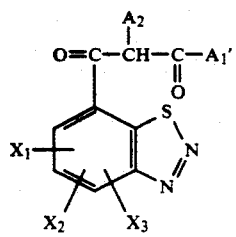

where the compounds of the formula I and Ia can also exist in the enol forms of the formula Ia'

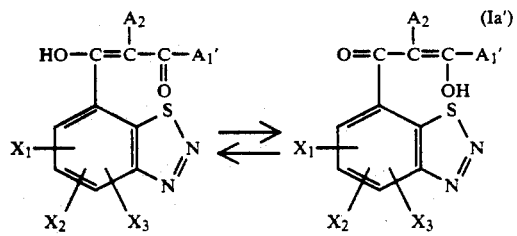

(Ia')

or

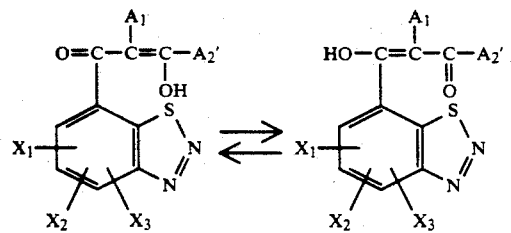

and in which $X_1$, $X_2$, $X_3$, $A_1$, $A_2$, $A_1'$ and $A_2'$ are as defined in formula I, II and IV, and $A_1$ and $A_2'$, or $A_1'$ and $A_2$, together are $C_1$-$C_3$alkylene-$(X)_n$CO, or $C_1$-$C_3$alkylene-$(X)_n$CO which is substituted by $C_1$-$C_4$alkyl-COOR, COOR, CON($R_2$), cyano or phenyl, or are N(R)—CO—N(R)—CO, in which R is hydrogen, $C_1$-$C_6$alkyl, $C_3$-$C_6$alkenyl or $C_3$-$C_6$alkynyl.

The following inert solvents are suitable for use in the above-described processes: aliphatic, cycloaliphatic or aromatic hydrocarbons, for example hexane, cyclohexane, toluene, xylene, petroleum ether or ligroin; chlorinated hydrocarbons, for example methylene chloride, chloroform, carbon tetrachloride, chlorobenzene; ethers, for example diethyl ether, diisopropyl ether, furan, tetrahydrofuran, dioxane; ketones, for example acetone, methyl ethyl ketone; alcohols, for example methanol, ethanol, isopropanol; esters, for example ethyl acetate, butyl acetate; nitriles, for example acetonitrile, propionitrile; acid amides, for example dimethylformamide; sulfones and sulfoxides, for example dimethyl sulfoxide and sulfolane.

Suitable bases or acid binders are hydroxides, carbonates, hydrogen carbonates or alcoholates of the alkali metals; and also tertiary amines, for example trialkylamine, pyridine or 4-N,N-dialkylaminopyridine.

Other substances which are used in the above-described processes are Lewis acids, for example the halides of boron, aluminium, magnesium, zinc, antimony, mercury, copper or silver.

The corresponding salts or complexes of the compounds of the formula I and Ia can be obtained by addition of metal salts, for example those with the cations $Mg^{2+}$, $Ca^{2+}$, $Ba^{2+}$, $Cu^{2+}$, $Ni^{2+}$, $Fe^{2+}/Fe^{3+}$, $Zn^{2+}$, $Sn^{2+}$ or $Mn^{2+}$, or by addition of inorganic or organic bases. In so far as they are agriculturally acceptable, they also form part of the invention.

The above-described processes correspond to methods for synthesis which are known from the literature. For example, they are described in U.S. Pat. No. 4,946,981.

Surprisingly, it has now been found that the attack of plants by injurious microorganisms and thus damage to the plants caused by the attack can be prevented by using the compounds of the formula I according to the invention. It is characteristic of the active ingredients according to the invention that protection of the plants can be effected by direct action on the plant-injurious microorganisms by means of foliar application or soil application as well as by activation and stimulation of the defence system of the plant (immunisation). The great advantage of the compounds of the formula I is the guarantee that the plants which have been treated with these substances remain healthy during the vegetation period on their own account without the use of further microbicidal substances. Accordingly, undesirable side-effects as can occur in the direct control of parasites with chemical substances, for example on the one hand by damage to the useful plants (phytotoxicity) and, on the other hand, by causing resistance in the injurious microorganisms, can be avoided by using the active ingredients according to the invention which advantageously results in entirely troublefree growth of the useful plants.

Extensive protection of the plants against diseases can be achieved due to the particular mode of action of the compounds of the formula I according to the invention, namely, on the one hand, the possibility of a direct control of the plant pathogens and, on the other hand, a generally increased readiness for defence of the plants treated with these active ingredients due to immunisation. The use of the active ingredients according to the invention is therefore particularly suitable for conditions as they are found in practice. Moreover, the systemic activity of the compounds of the formula I causes the protective effect also to be extended to newly-forming parts of the treated plants.

The general crop-protecting activity of the active ingredients according to the invention acts, for example, against the phytopathogenic fungi of the following classes: Fungi imperfecti (for example Botrytis, Helminthosporium, Fusarium, Septoria, Cercospora and Alternaria); Basidiomycetes (for example Hemileia, Rhizoctonia, Puccinia); Ascomycetes (for example Venturia, Podosphaera, Erysiphe, Monilinia, Uncinula).

Moreover, the active ingredients can be used particularly advantageously against the following noxious organisms: fungi, for example Oomycetes (for example

*Plasmopara viticola, Phytophthora infestans, Peronospora tabacina,* Pseudoperonospora, *Bremia letucae*), Fungi imperfecti (for example *Colletotrichum lagenarium, Pyricularia oryzae, Cercospora nicotinae*), Ascomycetes (for example *Venturia inaequalis*); bacteria, for example Pseudomonadaceae (*Pseudomonas lachrymans, Pseudomonas tomato, Pseudomonas tabaci*); Xanthomonadaceae (for example *Xanthomonas oryzae, Xanthomonas vesicatoria*); Erwinia (for example *Erwinia amylovora*); and viruses, for example the *tobacco mosaic* virus.

The compounds according to the invention can be used for protecting plants of various crops of useful plants.

Examples of plant species which are suitable within the scope of the invention for the use of the compounds of the formula I according to the invention are: cereals (wheat, barley, rye, oats, rice, sorghum and related species); beet (sugar beet and fodder beet); pomaceous fruit, stone fruit and soft fruit (apples, pears, plums, peaches, almonds, cherries, strawberries, raspberries and blackberries); pulses (beans, lentils, peas, soyabeans); oil crops (oil seed rape, mustard, poppy, olives, sunflowers, coconut, castor-oil plant, cacao, groundnuts); cucurbits (pumpkin, cucumbers, melons); fibre plants (cotton, flax, hemp, jute); citrus fruit (oranges, lemons, grapefruit, tangerines); vegetables (spinnach, lettuce, asparagus, cabbage species, carrots, onions, tomatoes, potatoes, bell peppers); Lauraceae (avocado, cinnamon, camphor) or plants such as maize, tobacco, nuts, coffee, sugar cane, tea, grapevines, hops, Musaceae and latex plants, as well as ornamental plants (flowers, shrubs, deciduous trees and coniferous trees, such as conifers).

This enumeration is not limiting.

Particularly suitable target crops for the use of the compounds of the formula I according to the invention are the following plants: cucumber, tobacco, grapevines, rice, pepper, potatoes, tomatoes, wheat, barley, pears and apples.

A particular advantage of the compounds of the formula I according to the invention is, besides their targeted activities in crop protection, the absence of phytotoxic properties.

The microbicidal compositions, used within the scope of the invention, for protecting plants against diseases, which contain the compounds of the formula I as active ingredients, are to be regarded as part of the invention.

Active ingredients of the formula I are customarily used in the form of combinations and can be applied to the plant or its environment simultaneously or in succession with other active ingredients. These other active ingredients can be fertilisers, trace element promoters or other preparations which have an effect on the growth of plants. However, they can also be selective herbicides, insecticides, fungicides, bactericides, nematicides, molluscicides or mixtures of a plurality of these preparations, if appropriate together with other carriers conventionally used in the art of formulation, surfactants or other application-enhancing additives.

Suitable carriers and additives can be solid or liquid and are those substances which are expedient in the art of formulation, for example natural or regenerated mineral substances, solvents, dispersants, wetting agents, adhesives, thickeners, binders or fertilisers.

One process for applying an active ingredient of the formula I, or an agrochemical composition comprising at least one of these active ingredients, is applying it to the plant (foliar application). Alternatively, the active ingredients of the formula I can reach the plant via the soil through the root system (soil application), by drenching the locus of the plant with a liquid preparation or incorporating the substances into the soil in solid form, for example in the form of granules. Alternatively, the compounds of the formula I can be applied to seeds (coating), either by soaking the grains in a liquid preparation of the active ingredient or by coating them with a solid preparation (seed dressing). Moreover, other types of application are possible in specific cases, for example the targeted treatment of the stalks of the plants, or of the buds.

The compounds of the formula I are employed as pure active ingredients or, preferably, together with auxiliaries conventionally used in the art of formulation. To this end, they are processed in a known manner to give, for example, emulsion concentrates, spreadable pastes, directly sprayable or dilutable solutions, dilute emulsions, wettable powders, soluble powders, dusts, granules, and also encapsulations, for example in polymer substances. The application methods, such as spraying, atomising, dusting, scattering, painting on or pouring as well as the nature of the compositions are selected to suit the intended aims and the prevailing circumstances. Advantageous application rates are generally 50 g to 5 kg of active ingredient (A.I.) per ha; preferably 100 g to 2 kg of A.I./ha, in particular 100 g to 600 g of A.I./ha.

The formulations, i.e. the compositions, preparations or combinations comprising the active ingredient of the formula I and, if desired, a solid or liquid additive, are prepared by intimately mixing and/or grinding the active ingredients with extenders, for example with solvents, solid carriers and, if appropriate, surface-active compounds (surfactants).

The following are possible as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones such as cyclohexanone, strongly polar solvents, such as N-methyl-2-pyrrolidone, dimethyl sulfoxide or dimethylformamide; and also epoxidised or unepoxidised vegetable oils, such as epoxidised coconut oil or soya oil; or water.

Solid carriers which are generally used, for example for dusts and dispersible powders, are ground natural minerals, such as calcite, talc, kaolin, montmorillonite or attapulgite. To improve the physical properties, it is also possible to add highly-disperse silica or highly-disperse absorptive polymers. Possible particulate, adsorptive carriers for granules are either porous types, for example pummice, brick grit, sepiolite or bentonite, or non-sorptive carrier materials, for example calcite or sand. Moreover, a large number of pregranulated materials of inorganic or organic nature can be used, such as, in particular, dolomite or comminuted plant residues.

Suitable surface-active compounds are non-ionic, cationic and/or anionic surfactants having good emulsifying, dispersing and wetting properties, depending on the nature of the active ingredient of the formula I to be formulated. Surfactants are also to be understood as meaning mixtures of surfactants.

Cationic surfactants are mainly quaternary ammonium salts which have at least one alkyl radical having 8 to 22 carbon atoms as N substituent, and lower, optionally halogenated alkyl radicals, benzyl radicals or lower hydroxyalkyl radicals as further substituents.

Suitable anionic surfactants can be either so-called water-soluble soaps or water-soluble synthetic surface-active compounds.

Suitable soaps which may be mentioned are the alkali metal salts, alkaline earth metal salts or substituted or unsubstituted ammonium salts of higher fatty acids ($C_{10}$–$C_{22}$), for example the sodium or potassium salts of oleic or stearic acid or of natural mixtures of fatty acids which can be obtained, for example, from coconut oil or tallow oil.

Synthetic surfactants which can be used are, in particular, fatty alcohol sufonates, fatty alcohol sulfates, sulfonated benzimidazole derivatives or alkylsulfonates. The fatty alcohol sulfonates or fatty alcohol sulfates generally exist in the form of alkali metal salts, alkaline earth metal salts or substituted or unsubstituted ammonium salts and have an alkyl radical having 8 to 22 carbon atoms.

Suitable non-ionic surfactants are mainly polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

The compositions can also comprise further additives such as stabilisers, defoamers, viscosity regulators, binders, adhesives as well as fertilisers or other active ingredients for achieving specific effects.

As a rule, the agrochemical preparations comprise 0.1 to 99% by weight, in particular 0.1 to 95% by weight, of active ingredient of the formula I, 99.9 to 1% by weight, in particular 99.8 to 5% by weight, of a solid or liquid additive, and 0 to 25% by weight, in particular 0.1 to 25% by weight, of a surfactant.

The examples which follow are intended to illustrate the invention without imposing any restriction.

EXAMPLE 1.1

Preparation of 3-(benzo-1,2,3-thiadiazole-7-carbonyloxy)-5,5-dimethyl-cyclohex-2-enone (intermediate)

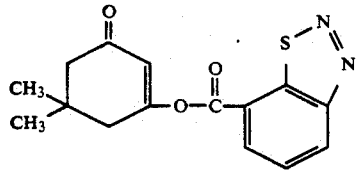

5.6 g (0.04 mol) of 5,5-dimethyl-1,3-cyclohexanedione are dissolved in a mixture of 4.4 g (0.044 mol) of triethylamine and 120 ml of ethyl acetate. 8.7 g (0.044 mol) of benzothiadiazole-7-carboxylic acid chloride are added dropwise at 15° to 20° C., and the mixture is subsequently stirred overnight at room temperature. The ethyl acetate solution is washed with $H_2O$, dried and concentrated. Purification by column chromatography using ethyl acetate/hexane gives 10.5 g (87.5%) of the title compound, melting point 131°–133° C.

| | Elemental analysis | | | |
|---|---|---|---|---|
| | C | H | N | S |
| found | 59.8 | 4.7 | 9.2 | 10.6 |
| calc. | 59.59 | 4.67 | 9.27 | 10.61 |

EXAMPLE 1.2

Preparation of 2-(benzo-1,2,3-thiadiazole-7-carbonyl)-5,5-dimethyl-1,3-cyclohexanedione

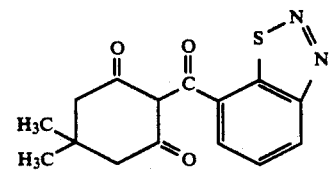

8.5 g of 3-(benzo-1,2,3-thiadiazole-7-carbonyloxy)-5,5-dimethyl-cyclohex-2-enone (Example 1.1), 0.09 g of KCN and 2.8 g of triethylamine are dissolved in 40 ml of dimethylformamide, and the solution is stirred overnight at room temperature. The reaction solution is poured into ice-water, acidified with concentrated HCl, and the product is filtered off with suction. 7.7 g (90.6%) of the title compound are obtained, melting point 168°–170° C.

| | Elemental analysis | | | |
|---|---|---|---|---|
| | C | H | N | S |
| found | 59.44 | 4.84 | 9.42 | 10.56 |
| calc. | 59.59 | 4.67 | 9.27 | 10.61 |

EXAMPLE 1.3

Preparation of 5-(benzo-1,2,3-thiadiazol-7-yl-2,2-dimethyl-1,3-dioxane-4,6-dione (2:1 salt with 4-dimethylaminopyridine)

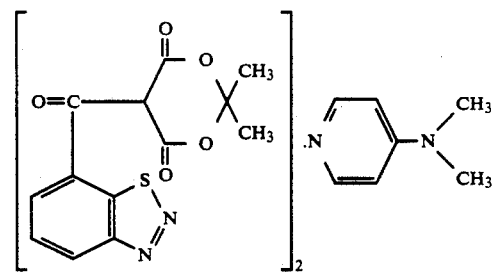

5.5 g of benzo-1,2,3-thiadiazole-7-carboxylic acid chloride in 10 ml of tetrahydrofuran are added dropwise to a solution, stirred at 0° C., of 3.6 g of cycloisopropylidene malonate, 7.6 ml of triethylamine and 2.0 g of 4-dimethylaminopyridine in 25 ml of dichloromethane. The reaction mixture is stirred for 2 hours at 0° C. and then applied directly to a silica gel column and extracted with ethyl acetate, resulting in the title compound in the form of a salt with 4-dimethylaminopyridine (2:1), m.p. 170°–172° C.

EXAMPLE 1.4

Preparation of diethyl 2-(benzo-1,2,3-thiadiazol-7-yl)malonate (Compound No. 4.15)

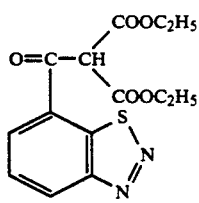

4.8 g of magnesium chloride in 50 ml of acetonitrile are treated with 7.6 ml of diethyl malonate and 14 ml of triethylamine, with ice-cooling and stirring. The mixture is stirred for 20 minutes and then treated at 0°–5° C. with portions of a suspension of 9.6 g of benzo-1,2,3-thiadiazole-7-carboxylic acid chloride in 50 ml of acetonitrile, the temperature being maintained at between 5° C. and 15° C. The resulting beige suspension is stirred for a further hour in an ice-bath at 0° C. and subsequently overnight at room temperature. On the next day, it is cooled again to 0° C., brought to pH 4.5 using 15% hydrochloric acid, and extracted with ethyl acetate. The extracts are dried over sodium sulfate, filtered over silica gel and evaporated. This results in the title compound in a yield of 83.2% of theory and with a melting point of 72°–74° C.

The compounds of Tables 1–7 are prepared analogously.

TABLE 1

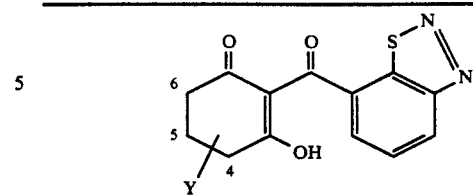

| Comp. No. | Y | physical data |
|---|---|---|
| 1.1 | H | m.p. 236–240° C. |
| 1.2 | 5,5-$(CH_3)_2$ | m.p. 168–170° C. |
| 1.3 | 5-$CH_3$ | m.p. 217–221° C. |
| 1.4 | 5-$C_2H_5$ | |
| 1.5 | 5-$C_3H_{7(i)}$ | m.p. 114–120° C. |
| 1.6 | 5-$C_4H_9$(tert.) | |
| 1.7 | 4,5,5-$(CH_3)_3$ | |
| 1.8 | 4-$CH_3$ | |
| 1.9 | 4-$CO_2CH_3$; 5,5-$(CH_3)_2$ | |
| 1.10 | 4-$CO_2CH_3$; 5-$C_3H_{7(i)}$ | |

TABLE 1-continued

| Comp. No. | Y | physical data |
|---|---|---|
| 1.11 | 4-CN; 5,5-$(CH_3)_2$ | |
| 1.12 | 5-phenyl | m.p. 165–169° C. |
| 1.13 | 5-$CO_2CH_3$ | |
| 1.14 | 5-$CO_2C_2H_5$ | m.p. 122° C. (decomp.) |
| 1.15 | 5-COOH | m.p. 205–208° C. |
| 1.16 | 5-$CON(CH_3)_2$ | |

TABLE 2

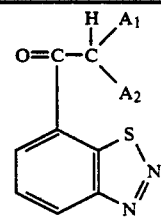

(Ph = phenyl)

| Comp. No. | $A_1$—$A_2$ | physical data |
|---|---|---|
| 2.1 | —$COOCH_2OOC$— | |
| 2.2 | —$COOC(CH_3)_2OOC$— | Decomp. 230° C. |
| 2.3 | —$COOC(C_2H_5)_2OOC$— | |
| 2.4 | —COOCH(Ph)OOC— | |
| 2.5 | —$COOCH_2CO$— | m.p. 192–194° C. |
| 2.6 | —$COSCH_2CO$— | m.p. 190° C. |
| 2.7 | —$COCH_2CH_2CO$— | |
| 2.8 | —$CON(CH_3)CH_2CO$— | |
| 2.9 | —$COOC(CF_3)_2OOC$— | |
| 2.10* | —$COOC(CH_3)_2OOC$— | m.p. 170-2° C. |
| 2.11 | —$COSCH_2SOC$— | |
| 2.12 | —$CON(CH_3)CON(CH_3)CO$— | m.p. 174–176° C. |
| 2.13 | —CO—NH—CO—NH—CO— | |
| 2.14 | —CO—$N(C_2H_5)$—CO—$N(C_2H_5)$CO— | |
| 2.15 | —CO—$N(C_3H_{7}(i))$-CO—$N(C_3H_{7}(i))$-CO— | |

*Salt with 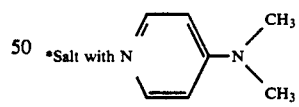

TABLE 3

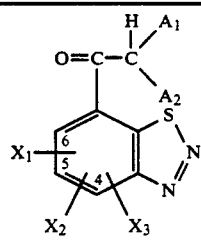

| Comp. No. | $X_1,X_2,X_3$ | $A_1$—$A_2$ | physical data |
|---|---|---|---|
| 3.1 | 6-Cl | —$CO(CH_2)_3CO$— | |
| 3.2 | 6-F | —$CO(CH_2)_3CO$— | m.p. 156–160° C. |
| 3.3 | 5-F | —$CO(CH_2)_3CO$— | |

TABLE 3-continued

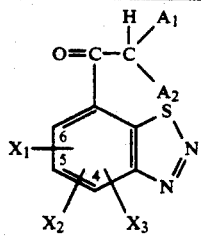

| Comp. No. | $X_1,X_2,X_3$ | $A_1-A_2$ | physical data |
|---|---|---|---|
| 3.4 | 5-Br | —COOCH$_2$OOC— | |
| 3.5 | 5-F | —COOC(CH$_3$)$_2$OOC— | |
| 3.6 | 6-SCH$_3$ | —COCH$_2$CH(CH$_3$)CH$_2$CO— | |
| 3.7 | 5-SCH$_3$ | —COOCH$_2$CO— | |
| 3.8 | 6-NO$_2$ | —COOCH$_2$CO— | |
| 3.9 | 5-NO$_2$ | —COOCH(COOCH$_3$)OOC— | |
| 3.10 | 5-J | —COCH$_2$CH(phenyl)CH$_2$CO— | |
| 3.11 | 6-F | —COSCH$_2$CO— | |
| 3.12 | 5-F | —CON(CH$_3$)CH$_2$CO— | |
| 3.13 | 4-F | —CO(CH$_2$)$_3$CO— | |
| 3.14 | 5-CH$_3$ | —CO(CH$_2$)$_2$CO— | |
| 3.15 | 4-F | —CON(CH$_3$)CON(CH$_3$)CO— | |
| 3.16 | 5-F | —CON(CH$_3$)CON(CH$_3$)CO— | |
| 3.17 | 6-F | —COCH$_2$CH(CH$_3$)CH$_2$CO— | |
| 3.18 | 6-F | —COCH$_2$CH(CH$_3$)CH$_2$CO— | |
| 3.19 | 5-F | —COCH$_2$CH(CH$_3$)CH$_2$CO— | |
| 3.20 | 4-F | —COCH$_2$CH(COOCH$_3$)CH$_2$CO— | |
| 3.21 | 4,6-di-F | —CO(CH$_2$)$_3$CO— | |
| 3.22 | 4,5-di-F | —COOCH$_2$CO— | |
| 3.23 | 5,6-di-F | —COCH$_2$CH(CH$_3$)—CH$_2$—CO— | |
| 3.24 | 4,5,6-tri-F | —CO(CH$_2$)$_3$CO— | |

TABLE 4

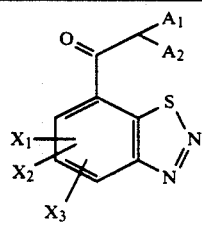

| Comp. No. | $X_1,X_2,X_3$ | $A_1$ | $A_2$ | physical data |
|---|---|---|---|---|
| 4.1 | H | CN | CN | |
| 4.2 | H | COOCH$_3$ | COOCH$_3$ | m.p. 140–142° C. |
| 4.3 | H | COOC$_4$H$_9$(tert.) | COOC$_4$H$_9$(tert.) | |
| 4.4 | H | COCH$_3$ | COCH$_3$ | m.p. 109–110° C. |
| 4.5 | H | CN | COOC$_2$H$_5$ | m.p. 117–119° C. |
| 4.6 | 6-Br | CON(CH$_3$)$_2$ | CON(CH$_3$)$_2$ | |
| 4.7 | 5-Cl | CON(CH$_2$—CH=CH$_2$)$_2$ | COCH$_3$ | |
| 4.8 | 5-NO$_2$ | COC$_2$H$_5$ | COC$_2$H$_5$ | |
| 4.9 | 5-F | COCH$_3$ | CN | |
| 4.10 | 6-F | CN | CN | |
| 4.11 | 6-F | COOC$_2$H$_5$ | COOC$_2$H$_5$ | m.p. 110–112° C. |
| 4.12 | 6-F | CN | COOC$_3$H$_7$(i) | |
| 4.13 | 5-F | CON(CH$_2$—CH≡CH)$_2$ | CON(CH$_2$—CH≡CH)$_2$ | |
| 4.14 | 4-F | COC$_3$H$_7$(i) | COC$_3$H$_7$(i) | |
| 4.15 | H | COOC$_2$H$_5$ | COOC$_2$H$_5$ | m.p. 72–74° C. |
| 4.16 | H | COCH$_3$ | COCH$_3$ | m.p. 117–119° C. |
| 4.17 | 4-F | COCH$_3$ | COCH$_3$ | |
| 4.18 | 4,6-di-F | COOC$_2$H$_5$ | COOC$_2$H$_5$ | |
| 4.19 | 4,5-di-F | COOC$_3$H$_7$(i) | COOC$_3$H$_7$(i) | |
| 4.20 | 5,6-di-F | COSCH$_3$ | COSCH$_3$ | |
| 4.21 | 4,5,6-tri-F | COCH$_3$ | COCH$_3$ | |
| 4.22 | H | COCF$_3$ | COOC$_2$H$_5$ | |
| 4.23 | H | COCF$_3$ | COCF$_3$ | |
| 4.24 | 4-F | COCF$_3$ | COOCH$_3$ | |

TABLE 5

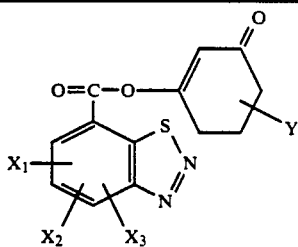

(intermediates)

| Comp. No. | Y | $X_1, X_2, X_3$ | physical data (m.p.) |
|---|---|---|---|
| 5.1 | H | H | 119–121° C. |
| 5.2 | 5,5-$(CH_3)_2$ | H | 131–133° C. |
| 5.3 | 5-$CH_3$ | H | 122–124° C. |
| 5.4 | 5-$C_2H_5$ | 6-F | |
| 5.5 | 5-$C_3H_7$(i) | H | Oil |
| 5.6 | 5-$C_4H_9$(tert.) | H | |
| 5.7 | 4,5,5-$(CH_3)_3$ | H | |
| 5.8 | 4-$CH_3$ | H | |
| 5.9 | 4-$CO_2CH_3$; 5,5-$(CH_3)_2$ | H | |
| 5.10 | 4-$CO_2CH_3$; 5-$C_3H_7$(i) | H | |
| 5.11 | 4-CN; 5,5-$(CH_3)_2$ | H | |
| 5.12 | 5-phenyl | H | 123–125° C. |
| 5.13 | 5-$CO_2CH_3$ | H | |
| 5.14 | 5-$CO_2C_2H_5$ | H | 83–85° C. |
| 5.15 | H | 6-F | |
| 5.16 | 5-$CON(CH_3)_2$ | H | |
| 5.17 | 5,5-$(CH_3)_2$ | 6-F | |
| 5.18 | 5,5-$(CH_3)_2$ | 5-F | |
| 5.19 | 5-$COOCH_3$ | 4-F | |
| 5.20 | H | 5-F | 132–134° C. |
| 5.21 | H | 4-F | 148–149° C. |
| 5.22 | 5-$C_2H_5$ | H | |
| 5.23 | 5-COOH | H | |
| 5.24 | H | 6-Cl | |
| 5.25 | 5-$CH_3$ | 6-$SCH_3$ | |
| 5.26 | 5-phenyl | 5-J | |
| 5.27 | 5-$CH_3$ | 6-F | |
| 5.28 | H | 4,5-di-F | |
| 5.29 | 5,5-$(CH_3)_2$ | 5,6-di-F | |
| 5.30 | H | 4,5,6-tri-F | |
| 5.31 | H | 4-Br-6-F | |
| 5.32 | H | 4,6-di-F | |

TABLE 6

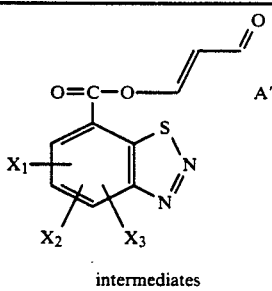

intermediates

| Comp. No. | CO A' | $X_1, X_2, X_3$ | physical data (m.p.) |
|---|---|---|---|
| 6.1 | CO—$CH_2$—$CH_2$ | H | 154–156° C. |
| 6.2 | CO—$CH_2$—$CH_2$ | 5-$CH_3$ | |
| 6.3 | CO—N($CH_3$)—$CH_2$ | 5-F | |
| 6.4 | CO—S—$CH_2$ | 6-F | |
| 6.5 | CO—O—$CH_2$ | 6-$NO_2$ | |
| 6.6 | CO—O—$CH_2$ | 5-$SCH_3$ | |
| 6.7 | CO—N($CH_3$)—$CH_2$— | H | |
| 6.8 | CO—S—$CH_2$ | H | |
| 6.9 | CO—O—$CH_2$ | H | |
| 6.10 | CO—$OCH_2$ | 4,5-di-F | |
| 6.11 | CO—$SCH_2$ | 4,5,6-tri-F | |

TABLE 7

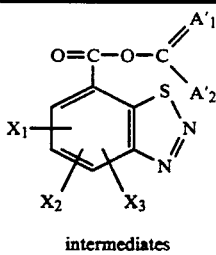

intermediates

| Comp. No. | $A'_1$ | $A'_2$ | $X_1, X_2, X_3$ | phys. data |
|---|---|---|---|---|
| 7.1 | $CHCOCH_3$ | $CH_3$ | H | |
| 7.2 | $CHCOC_2H_5$ | $C_2H_5$ | 5-$NO_2$ | |
| 7.3 | $CHCOC_3H_7$(i) | $C_3H_7$(i) | 4-F | |
| 7.4 | $CHCOOCH_3$ | $CF_3$ | H | |
| 7.5 | $CHCOOC_4H_9$(tert.) | $CF_3$ | H | |
| 7.6 | $CHCOOC_2H_5$ | $CF_3$ | 6-F | |
| 7.7 | $CHCOCF_3$ | $CF_3$ | H | |
| 7.8 | $CHCOOCH_3$ | $CH_3$ | H | |
| 7.9 | $CHCOCH_3$ | $CH_3$ | 4-F |
| 7.10 | $CHCON(CH_2CH=CH_2)_2$ | $CH_3$ | 5-Cl | |
| 7.11 | CH—CN | $CH_3$ | 5-F | |
| 7.12 | CH—$COOCH_3$ | $CH_3$ | H | |
| 7.13 | CH—$COOCH_3$ | $CH_3$ | 4,5,6-tri-F | |

Formulation examples of active ingredients from the tables
(%=percent by weight)

| 2.1 Wettable powder | a) | b) | c) |
|---|---|---|---|
| Active ingredient from the tables | 25% | 50% | 75% |
| Sodium ligninsulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 mol of ethylene oxide) | — | 2% | — |
| Highly-disperse silica | 5% | 10% | 10% |
| Kaolin | 62% | 27% | — |

The active ingredient is mixed with the additives and ground in a suitable mill until homogeneous. This gives wettable powders which can be diluted with water to give suspensions of any desired concentration.

| 2.2 Emulsion concentrate | |
|---|---|
| Active ingredient from the tables | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| 2.3 Dusts | a) | b) |
|---|---|---|
| Active ingredient from the tables | 5% | 8% |
| Talc | 95% | — |
| Kaolin | — | 92% |

Ready-to-use dusts are obtained by mixing the active ingredient with the carriers and grinding the mixture in a suitable mill.

| 2.4 Extruder granules | |
|---|---|
| Active ingredient from the tables | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| 2.5 Coated granules | |
|---|---|
| Active ingredient from the tables | 3% |
| Polyethylene glycol (MW 200) | 3% |
| Kaolin | 94% |

(MW = molecular weight)

In a mixer, the finely-ground active ingredient is applied uniformly to the kaolin which has been moistened with polyethylene glycol. In this manner, dust-free coated granules are obtained.

| 2.6 Suspension concentrate | |
|---|---|
| Active ingredient from the tables | 40% |
| Ethylene glycol | 10% |
| Nonylphenol polyethylene glycol ether (15 mol of ethylene oxide) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely-ground active ingredient is mixed intimately with the additives. A suspension concentrate is obtained from which suspensions of any desired concentration can be prepared by dilution with water.

3. BIOLOGICAL EXAMPLES

Example 3.1: Activity against *Colletotrichum lagenarium* on *Cucumis sativus L.* a) Cucumber plants are grown for 2 weeks and then sprayed with a spray mixture prepared with a wettable powder of the active ingredient (concentration: 200 ppm). After 48 hours, the plants are infected with a spore suspension (1.5 × 10⁵ spores/ml) of the fungus and incubated for 36 hours at high atmospheric humidity and a temperature of 23° C. Incubation is then continued at normal atmospheric humidity and 22° C. to 23° C.

The protective action, based on the fungus infestation, is assessed 7-8 days after the infection.

b) Cucumber plants are grown for 2 weeks and then treated by soil application with a spray mixture prepared with a wettable powder of the active ingredient (concentration: 60 or 20 ppm, relative to the soil volume). After 48 hours, the plants are infected with a spore suspension (1.5 × 10⁵ spores/ml) of the fungus and incubated for 36 hours at high atmospheric humidity and a temperature of 23° C. The incubation is then continued at normal atmospheric humidity and 22° C.

The protective action, based on the fungus infestation, is assessed 7-8 days after the infection.

In tests (a) and (b), a good action is shown by compounds from Tables 1 to 7. For example, compounds 1.1, 1.2, 1.3, 1.5, 1.12, 1.14, 2.2, 2.5, 2.6, 2.12, 3.2, 3.13, 4.2, 4.4, 4.5, 4.14, 4.15, 4.16, 5.1, 5.2, 5.3, 5.12, 5.14, 5.21 and 6.1 reduce fungus infestation to 0 to 20%. In contrast, untreated, but infected control plants show an infestation with Colletotrichum of 100%.

Example 3.2: Action against *Phytophthora infestants* on tomato plants a) Tomato plants are grown for 3 weeks and then sprayed with a spray mixture prepared with a wettable powder of the active ingredient (0.02% active ingredient). After 24 hours, the treated plants are infected with a sporangia suspension of the fungus. The fungus infestation is assessed after incubation of the infected plants for 5 days at 90-100% relative atmospheric humidity and 20° C.

b) A spray mixture prepared with a wettable powder of the active ingredient is poured in the vicinity of tomato plants which have been grown for 3 weeks (0.006% active ingredient relative to the soil volume). Care is taken not to bring the aerial parts of the plants in contact with the spray mixture. After 48 hours, the treated plants are infected with a sporangia suspension of the fungus. The fungus infestation is assessed after incubation of the infected plants for 5 days at 90-100% relative atmospheric humidity and 20° C.

Compounds from Tables 1 to 7 show a good protective action against the Phytophthora fungus. For example, the fungus infestation is reduced to 0 to 20% by compounds 2.5, 4.15, 5.1, 5.14 and 6.1 in test (a) and by compounds 2.5, 3.2, 5.1, 5.12 and 6.1 in test (b). In contrast, untreated but infected control plants show a Phytophthora infestation of 100%.

Example 3.3: Action against *Pyricularia oryzae* on rice plants a) Rice plants are grown for 2 weeks and then sprayed with a spray mixture prepared with a wettable powder of the active ingredient (0.02% active ingredient). After 48 hours, the treated plants are infected with a conidia suspension of the fungus. The fungus infestation is assessed after incubation for 5 days at 95-100% relative atmospheric humidity and 24° C.

b) A spray mixture prepared with a wettable powder of the active ingredient is poured in the vicinity of 2-week-old rice plants (0.006% active ingredient relative to the soil volume). Hereinafter, the pots are filled with water to such an extent that the basal stem parts of the rice plants are submerged. After 96 hours, the treated rice plants are infected with a conidia suspension of the fungus. The fungus infestation is assessed after incubation of the infected plants for 5 days at 95-100% relative atmospheric humidity and approx. 24° C.

Compared with untreated control plants (100% infestation), the fungal infestation of rice plants which have been treated with a spray mixture comprising a compound from Tables 1 to 7 as active ingredient, is only slight. In test (a) for example, compound 1.1 reduces the infestation to 0 to 20%.

Example 3.4: Action against *Bremia lactucae* on lettuce

A formulated solution of the active ingredient (0.002% active ingredient relative to the soil volume) is poured in the vicinity of two-week-old lettuce plants. After 5 days, the treated plants are inoculated with a spore suspension of the fungus (5 × 10⁴ s/ml). The plants are incubated at 18° C., first under a hood (relative atmospheric humidity 90–100%) for 2 days and then for 7 days without a hood. To make the fungus sporulate, the plants are placed under a hood for a further 3 days.

12 days after inoculation, the fungus infestation is assessed on the basis of the leaf area infected with fungus.

Compounds from Tables 1 to 7 show a good action against Bremia. For example, plants which have been treated with compound 1.1 or 1.3 remain largely free from infestation (0–30% damage). In contrast, untreated but infected plants (control) show an infestation with Bremia of 100%.

Example 3.5: Action against *Erysiphe graminis* on wheat

Protective action: 17-day-old wheat plants are sprayed with a formulated solution of the active ingredient (0.02% active ingredient). Immediately after the treatment, the plants are incubated under cylinders. After 24 hours, the plants are uncovered. After a further 3 days, the treated plants are cut off above the primary leaf. The primary leaves are oriented horizontally and, in an inoculation chamber, inoculated with Erysiphe graminis spores (spore density: 0.2 mg per m$^2$). The test is carried out in a controlled-environment cabinet with 12 h light (18 kLux), 20° C. and 12 h darkness, 18° C.

The infestation is assessed 9 and 13 days after the inoculation.

In this test, compounds from Tables 1 to 7 used as active ingredient show a good action against *Erysiphe graminis*. For example, plants which have been treated with compound 1.1, 1.2, 1.3, 1.5, 1.12, 1.14, 1.15, 2.5, 2.12, 3.2, 4.2, 4.4, 4.5, 4.15, 4.16, 5.2, 5.3, 5.14 or 5.21, remain largely free from infestation with Erysiphe (0 to 20% damage). Untreated, but infected plants (control), in contrast, show an infestation with Erysiphe of 100%.

Example 3.6: Action against *Cercospora nicotianae* on tobacco plants

A) Foliar Application

Tobacco plants (8 weeks old) are sprayed with a formulated solution of the active ingredient (concentration: 200 ppm). Four days after the treatment, the plants are inoculated with a spore suspension of *Cercospora nicotianae* (10$^5$ spores/ml) and incubated for 5 days at high atmospheric humidity and a temperature of 22°–25° C. The incubation is then continued at normal atmospheric humidity and at 20°–22° C.

B) Soil Application

Tobacco plants (8 weeks old) are treated by soil application with a formulated solution of the active ingredient (concentration: 0.002% active ingredient). After 4 days, the plants are inoculated with a spore suspension of *Cercospora nicotianae* (10$^5$ spores/ml) and incubated for 5 days at high atmospheric humidity and a temperature of 22°–25° C. The incubation was then continued at normal atmospheric humidity and at 20°–22° C.

In tests A and B, the symptoms are assessed 12 to 14 days after the infection, based on the fungus infestation.

The control plants show an infestation of 100%. Plants which have been treated with compound 1.1, 1.2, 1.3, 1.12, 1.14, 1.15, 2.5, 4.2, 4.4, 4.5, 4.15, 4.16, 5.2, 5.3, 5.12 or 5.14, for example in test A, show an infestation of 0–20%.

Example 3.7: Action against *Cercospora arachidicola* on groundnut plants

10–15 cm high groundnut plants are sprayed with a spray mixture prepared with a wettable powder of the active ingredient (0.02% active ingredient) and, after 48 hours, infected with a conidia suspension of the fungus. The infected plants are incubated for 72 hours at approx. 21° C. and high atmospheric humidity and subsequently placed in a greenhouse until the typical foliar lesions appear. The fungicidal action is assessed 12 days after the infection and based on number and size of the lesions which appear.

Compared with untreated, but infected control plants (number and size of lesions=100%), groundnut plants which have been treated with active ingredients from Tables 1 to 7 show a greatly reduced infestation with Cercospora. In the above tests, for example, compounds Nos. 3.2 and 5.3 largely prevented the appearance of lesions (0–20%).

Example 3.8: Action against *Puccinia graminis* on wheat Residual-protective action 6 days after sowing, wheat plants are sprayed with a spray mixture prepared with a wettable powder of the active ingredient (0.02% active ingredient). After 24 hours, the treated plants are infected with a uredospore suspension of the fungus. After incubation for 48 hours at 95–100% relative atmospheric humidity and approx. 20° C., the infected plants are placed in a greenhouse at approx. 22° C. The development of rust pustules is assessed 12 days after the infection.

Untreated, but infected control plants show an infestation with Puccinia of 100%. Compounds from Tables 1 to 7 show a good action against Puccinia fungi.

For example, compounds nos. 1.1, 1.14, 1.15, 2.5, 2.6, 3.2, 4.4, 4.5, 4.16, 5.1 and 6.1 reduce the fungus infestation to below 20%.

Example 3.9: Action against *Pseudomonas lachrymans* on *Cucumis sativus* L.

A) Foliar Application

Cucumber plants are grown for 2 weeks and then sprayed with a spray mixture prepared with a wettable powder of the active ingredient (concentration: 0.02% active ingredient).

After 1 week, the plants are infected with a bacterial suspension (10$^8$ bacteria/ml) and incubated for 7 days at high atmospheric humidity and a temperature of 23° C.

The protective action is assessed 7–8 days after the infection, based on the infestation with bacteria.

Compounds from Tables 1 to 7 have a good protective effect against *Pseudomonas lachrymans*. Plants which have been treated, for example, with compound 1.1, 1.3, 1.12, 1.14, 1.15, 2.5, 3.2, 4.5, 4.15, 4.16, 5.3 or 5.14, remain largely free from Pseudomonas (infestation 20 to 0%).

B) Soil Application

Cucumber plants are grown for 2 weeks and then treated by soil application with a spray mixture prepared with a wettable powder of the active ingredient (concentration: 0.002% active ingredient relative to the soil volume).

After 1 week, the plants are infected with a bacterial suspension (10$^8$ bacteria/ml) and incubated for 7 days at a high atmospheric humidity and a temperature of 23° C.

The protective action is assessed 7–8 days after the infection, based on the infestation with bacteria.

Compounds from Tables 1 to 7 have a good immunising effect against *Pseudomonas lachrymans*. Plants which have been treated, for example, with compound 1.1, 1.2, 1.3, 1.12, 1.14, 1.15, 2.5, 3.2, 4.2, 4.4, 4.5, 4.15, 4.16, 5.2, 5.3, 5.12 or 5.14, remain virtually free from Pseudomonas (infestation 20 to 0%).

Untreated, but infected control plants show a disease level of 100% in tests A and B.

Example 3.10: Action against *Plasmopara viticola* on grapevines

Grapevine seedlings in the 4-5-leaf stage are sprayed with a spray mixture prepared with a wettable powder of the active ingredient (0.02% active ingredient). After 1 week, the treated plants are infected with a sporangia suspension ($5 \times 10^4$ sporangia/ml) of the fungus. The protective action is assessed after an incubation for 6 days at 95-100% relative atmospheric humidity and 20° C.

In this test, untreated but infected control plants show an infestation of 100%.

Compounds from Tables 1 to 7 have a good action against *Plasmopara viticola*, grapevines which have been treated with, for example, compound 2.5 or 5.1, remain largely free from *Plasmopara viticola* (infestation 20 to 0%).

Example 3.11: Action against *Pythium ultimum* on *Zea mays* (maize, cv. Sweet Corn)

Test principle: Soil fungus: protective, local soil application.

Test method: Mycelium of *Pythium ultimum* is mixed with soil (500 ml of mycelium suspension per 10 liters of soil) and 250 ml plastic dishes are filled with the fungus/soil mixture. After 4 days incubation at 10° C., 10 kernels of the test plant (maize) are introduced into each dish. On the next day, 50 ml portions of spray solutions, prepared with 25% wettable powder and water and comprising 20; 6; 2; 0.6; 0.2; 0.06 and 0.02 ppm of A.I., are poured over the prepared dishes. After a 7-day incubation phase at 10° C. followed by a 4-day incubation phase at 22° C., the action of the test substances is assessed by numerically evaluating the emergence of the test plants. Compounds from Tables 1 to 7 show a good action against *Pythium ultimum*. For example, compounds 2.5 or 4.5 show an action of over 80%.

Example 3.12: Action against *Peronospora tabacina* on tobacco plants

A) Foliar Application

Tobacco plants (8 weeks old) are sprayed with a formulated solution of the active ingredient (concentration: 0.02% active ingredient). Four days after the treatment, the plants are inoculated with a sporangia suspension of Peronospora tabacina ($10^4$ sporangia/ml), kept for 20 hours in the dark at 25° C. and high atmospheric humidity, whereupon incubation is continued in a normal day/night sequence.

B) Soil Application

Tobacco plants (8 weeks old) are treated by soil application with a formulated solution of the active ingredient (concentration: 0.006% active ingredient relative to the soil volume). After 4 days, the plants are inoculated with a sporangia suspension of *Peronospora tabacina* ($10^4$ sporangia/ml), kept for 20 hours in the dark at 25° C. and high atmospheric humidity, whereupon incubation is continued in a normal day/night sequence.

In tests A and B, the assessment of the symptoms is based on the leaf area infested with fungus.

The control plants show an infestation of 90 to 100%. Plants which have been treated with compound 1.1 in test A show an infestation of 0-30%.

What is claimed is:

1. A compound of the formula I

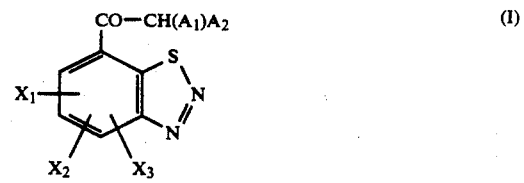

in which $A_1$ and $A_2$ independently of one another are CO—C$_1$-C$_4$alkyl, COO—C$_1$-C$_4$alkyl, CO—CF$_3$, CO—N(R)$_2$ or cyano;

the combination of $A_1$ and $A_2$ is CO(X)$_n$—C$_1$-C$_3$alkylene-(X)$_n$CO, CO(X)$_n$—C$_1$-C$_3$alkylene-(X)$_n$CO which is substituted by C$_1$—C$_4$alkyl, COOR, CON(R)$_2$, cyano or phenyl, it being possible for the phenyl ring, in turn, to be substituted by halogen, methyl, trifluoromethyl, methoxy, nitro or cyano; CO—N(R)—CO—N(R)—CO;

R is hydrogen, C$_1$-C$_6$alkyl, C$_3$-C$_6$alkenyl or C$_3$-C$_6$alkynyl;

X is oxygen, sulfur or N(CH$_3$);

$X_1$, $X_2$ and $X_3$ independently of one another are hydrogen, halogen, methyl, methylthio, methoxy or nitro;

n is 0 or 1;

including a salt of the compound of the formula I with agriculturally acceptable organic or inorganic bases, including a metal complex.

2. A compound according to claim 1, of the formula I, in which:

the combination of $A_1$ and $A_2$ is CO(X)$_n$—C$_1$-C$_3$alkylene-(X)$_n$CO, or CO—C$_1$-C$_3$alkylene-CO which is substituted by C$_1$-C$_4$alkyl, COOH, COOCH$_3$, COOC$_2$H$_5$, COOCH$_2$—CH=CH$_2$, COOCH$_2$—C≡CH, phenyl, the group CO—N(CH$_3$)$_2$ or cyano; CO—N(R')—CO—N(R')—CO;

R' is hydrogen or C$_1$-C$_3$alkyl;

X is oxygen or sulfur;

$X_1$, $X_2$ and $X_3$ independently of one another are hydrogen, F, methyl, methoxy, methylthio or nitro;

n is 0 or 1;

including a salt of the compound of the formula I with organic or inorganic bases, or including a metal complex with Mg, Ca, Ba, Sn, Fe, Zn, Cu, Ni or Mn.

3. A compound according to claim 1, of the formula I, in which $A_1$ and $A_2$ independently of one another are CO—C$_1$-C$_4$alkyl, COO—C$_1$-C$_4$alkyl, CO—CF$_3$, CO—N(R)$_2$ or cyano;

R is hydrogen, C$_1$-C$_6$alkyl, C$_3$-C$_6$alkenyl or C$_3$-C$_6$alkynyl;

$X_1$, $X_2$, and $X_3$ independently of one another are hydrogen, halogen, methyl, methylthio, methoxy or nitro;

including a salt of the compound of the formula I with agriculturally acceptable organic or inorganic bases or including a metal complex with Mg, Ca, Ba, Cu, Sn, Fe, Zn, Ni or Mn.

4. A compound of the formula I according to claim 2, in which:

the combination of $A_1$ and $A_2$ is $CO(X)_n$—$C_1$-$C_3$alkylene-$(X)_n CO$, or $CO(X)_n$—$C_1$-$C_3$alkylene-$(X)_n CO$ which is substituted by $C_1$-$C_4$alkyl, COOH, COOCH$_3$, phenyl or the group CO—N(CH$_3$)$_2$;

X is oxygen;

$X_1$, $X_2$, and $X_3$ independently of one another are hydrogen, fluorine or methyl;

n is 0 or 1.

5. A compound of the formula I according to claim 3, in which:

$A_1$ and $A_2$ independently of one another are CO—C$_1$-C$_2$alkyl, COO—C$_1$-C$_2$alkyl, CO—CF$_3$ or CO—N(C$_1$-C$_2$alkyl)$_2$;

$X_1$, $X_2$, and $X_3$ independently of one another are hydrogen, fluorine or methyl.

6. A compound of the formula I according to claim 4, in which:

the combination of $A_1$ and $A_2$ is CO—C$_1$-C$_3$alkylene-CO, or CO—C$_1$-C$_3$alkylene-CO which is substituted by C$_1$-C$_2$alkyl, COOH or phenyl;

$X_1$, $X_2$, and $X_3$ independently of one another are hydrogen or fluorine.

7. A compound of the formula I according to claim 5, in which:

$A_1$ and $A_2$ independently of one another are CO—C$_1$-C$_2$alkyl, COO—C$_1$-C$_2$alkyl or CO—N(CH$_3$)$_2$;

$X_1$, $X_2$, and $X_3$ independently of one another are hydrogen or fluorine.

8. A compound of the formula I according to claim 6, in which: the combination of $A_1$ and $A_2$ is CO—C$_1$-C$_3$alkylene-CO, or CO—C$_1$-C$_3$alkylene-CO which is substituted by methyl;

$X_1$, $X_2$ and $X_3$ independently of one another are hydrogen or fluorine.

9. A compound of the formula I according to claim 3, in which:

$A_1$ and $A_2$ independently of one another are CO—CH$_3$, COOC$_1$-C$_4$alkyl, CN or CON(CH$_2$C≡CH)$_2$;

$X_1$, $X_2$, and $X_3$ independently of one another are hydrogen or fluorine.

10. A compound of the formula I according to claim 2, in which:

the combination of $A_1$ and $A_2$ is CO—N(R')—CO—N(R')—CO;

R' is hydrogen or C$_1$-C$_3$alkyl;

$X_1$, $X_2$ and $X_3$ independently of one another are hydrogen, fluorine or methyl.

11. A compound of the formula I according to claim 10, in which:

the combination of $A_1$ and $A_2$ is CO—N(CH$_3$)—CO—N(CH$_3$)—CO;

$X_1$, $X_2$ and $X_3$ independently of one another are hydrogen or fluorine.

12. A compound of the formula I according to claim 1, selected from the group consisting of:

2-(benzo-1,2,3-thiadiazole-7-carbonyl)-3-hydroxy-cyclohex-2-enone;

2-(benzo-1,2,3-thiadiazole-7-carbonyl)-3-hydroxy-5,5-dimethyl-cyclohex-2-enone;

2-(benzo-1,2,3-thiadiazole-7-carbonyl)-3-hydroxy-5-methyl-cyclohex-2-enone;

2-(benzo-1,2,3-thiadiazole-7-carbonyl)-3-hydroxy-5-isopropyl-cyclohex-2-enone;

2-(benzo-1,2,3-thiadiazole-7-carbonyl)-3-hydroxy-5-phenyl-cyclohex-2-enone;

2-(6-fluoro-benzo-1,2,3-thiadiazole-7-carbonyl)-3-hydroxy-5,5-dimethyl-cyclohex-2-enone;

2-(4-fluoro-benzo-1,2,3-thiadiazole-7-carbonyl)-3-hydroxy-cyclohex-2-enone;

5-(benzo-1,2,3-thiadiazole-7-carbonyl)-1,3-dimethyl-2,4,6-1H,3H,5H-pyrimidinetrione; diethyl (benzo-1,2,3-thiadiazole-7-carbonyl)malonate.

13. A composition for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises, as active component, an infestation-controlling or infestation-preventing amount of one or more compounds of the formula I according to claim 1, together with a suitable carrier material.

14. A composition for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises, as active component, an infestation-controlling or infestation-preventing amount of one or more compounds of the formula I according to claim 2, together with a suitable carrier material.

15. A composition for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises, as active component, an infestation-controlling or infestation-preventing amount of one or more compounds of the formula I according to claim 3, together with a suitable carrier material.

16. A composition for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises, as active component, an infestation-controlling or infestation-preventing amount of one or more compounds of the formula I according to claim 4, together with a suitable carrier material.

17. A composition for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises, as active component, an infestation-controlling or infestation-preventing amount of one or more compounds of the formula I according to claim 12, together with a suitable carrier material.

18. A process for controlling or preventing infestation of crop plants by fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus, which comprises applying, as active ingredient, an infestation-controlling or infestation-preventing amount of a compound of the formula I according to claim 1 to the plant, parts of the plant or its locus.

19. A process for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus which comprises applying, as active ingredient, an infestation-controlling or infestation-preventing amount of a compound according to claim 2 to the plant, parts of the plant or its locus.

20. A process for controlling or preventing infestation from fungi selected from the classes consisting of Oomycetes, *Fungi imperfecti*, Basidiomycetes and Ascomycetes, bacteria selected from Pseudomonadaceae, Xanthomonadaceae and Erwinia, and the tobacco mosaic virus which comprises applying, as active ingredient, an infestation-controlling or infestation-preventing amount of a compound according to claim 12 to the plant, parts of the plant or its locus.

21. A process according to claim 18, wherein the infestation controlled is fungi selected from the classes consisting of Oomycetes, *Fungi imperfecti*, Basidiomycetes and Ascomycetes.

* * * * *